United States Patent
Pak et al.

(10) Patent No.: US 6,809,201 B2
(45) Date of Patent: Oct. 26, 2004

(54) INTERCALATOR SUITABLE FOR ELECTROCHEMICAL DETECTION OF DOUBLE STRAND DNAS AND A PROCESS FOR PREPARING THEREOF

(75) Inventors: Youngmi Kim Pak, Kunpo-si (KR); James Jungho Pak, Kunpo-si (KR); Sanghee Kim, Seoul (KR); Hong-Kyu Lee, Seoul (KR)

(73) Assignee: Mitocon Ltd. (KR)

( * ) Notice: Subject to any disclaimer, the term of this patent is extended or adjusted under 35 U.S.C. 154(b) by 328 days.

(21) Appl. No.: 09/927,852

(22) Filed: Aug. 10, 2001

(65) Prior Publication Data

US 2002/0117396 A1 Aug. 29, 2002

(30) Foreign Application Priority Data

Feb. 20, 2001 (KR) .......................................... 2001-8467

(51) Int. Cl.[7] .......................... C07F 17/02; C07D 15/02
(52) U.S. Cl. ........................................ 544/361; 556/145
(58) Field of Search ........................... 544/361; 556/145

(56) References Cited

U.S. PATENT DOCUMENTS 6,368,807 B2 * 4/2002 Makino et al. ................. 435/6

FOREIGN PATENT DOCUMENTS

EP         1 106 619 A2 *  6/2001

OTHER PUBLICATIONS

Takenaka et al., Chem. Commun., 1111, 1998.*
Takenaka et al., Anal. Chem. 72, 1334–1341, 2000.*

* cited by examiner

Primary Examiner—Venkataraman Balasubramanian
(74) Attorney, Agent, or Firm—Anderson Kill & Olick, PC

(57) ABSTRACT

The present invention relates to the compound of formula (I) useful as an intercalator in electrochemical detection of double-stranded DNAs, and a method for preparation thereof:

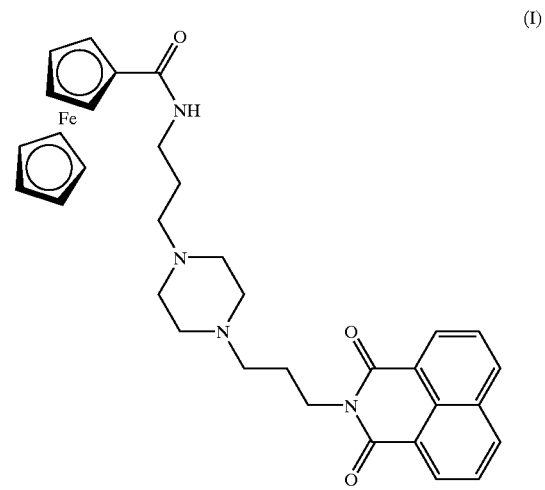

2 Claims, 2 Drawing Sheets

INTERCALATOR SUITABLE FOR ELECTROCHEMICAL DETECTION OF DOUBLE STRAND DNAS AND A PROCESS FOR PREPARING THEREOF

FIELD OF THE INVENTION

The present invention relates to novel intercalators suitable for electrochemical detection of double strand DNAs (dsDNA), and a process for preparing thereof.

BACKGROUND OF THE INVENTION

DNA chips have been widely used in gene and molecular biology researches such as the measurement of RNA expression in a large scale, detection of mutant genome DNAs, gene diagnosis, pharmacogenomics and medicine, as they can detect RNAs or DNAs contained in a sample much more efficiently than the conventional Southern blot or Northen blot method.

Generally, DNA chips detect a target DNA, for example, by way of accumulating hundreds of thousands of probe DNA fragments, each having a specified base sequence, on a very small chip surface, contacting the probe DNA fragments with a single strand of the target DNA labeled with a fluorescent material to induce hybridization, and identifying the hybridized DNA by laser irradiation.

However, the above method has the disadvantages that it requires the use of an expensive optical apparatus including a laser scanner and the cost of fluorescent labeling is high. Further, it is difficult to quantitatively determine the amount of the target DNA in a sample from the luminescent intensity.

Accordingly, there have been numerous efforts to solve the above-mentioned problems. For instance, Clinical Microsensors Inc. suggests a method of detecting a DNA by binding a redox-active material, e.q., a transition metal complex on a selected site of a single-stranded probe DNA, bringing a single-stranded target DNA into contact with the resulting probe DNA to induce hybridization, and measuring the change in the electron transporting rate attributable to the hybridization. In addition, Japanese Patent Publication No. 2000-125865 provides a method of detecting a gene of a specimen DNA by allowing a single-stranded sample DNA to interact with a single strand probe DNA immobilized on an electrode surface in the presence of an electrochemically active intercalator, e.g., N-N-bis[[4-(3-ferrocenecarboxaminopropyl)piperazinyl]propyl] naphthalene-1,4,5,8-tetracarboxylic acid, to form a hybridized DNA carrying the intercalator, followed by determining the current which flows through the intercalator.

These methods, however, still exhibit a limited sensitivity for quantitative DNA detection, and thus, there has existed a need to develop an improved intercalator that can be used in a DNA detection method having a higher sensitivity.

SUMMARY OF THE INVENTION

Accordingly, it is an object of the present invention to provide a novel intercalator suitable for detection double strand DNAs with a high sensitivity.

It is another object of the present invention to provide a process for preparing the inventive compound.

It is another object of the present invention to provide a novel intermediate used in said process.

In accordance with one aspect of the present invention, there is provided N-[3-[4-(3-ferrocenecarboxamidopropyl)piperazinyl]-propyl]-1,8-naphthalene imide of formula (I):

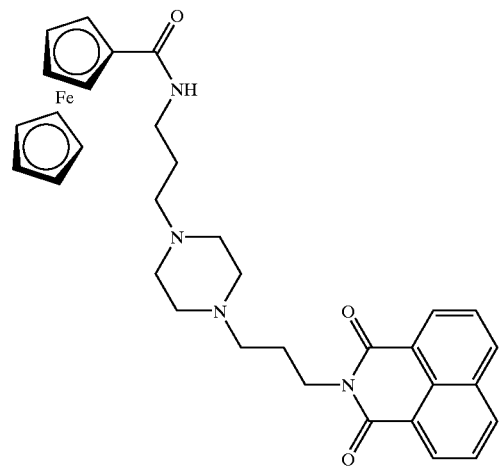

In accordance with another aspect of the present invention, there is provided a process for preparing the compound of formula (I) comprising reacting the compound of formula (III) with 1,4-bis(3-aminopropyl)piperazine in an organic solvent to obtain the compound of formula (II), and reacting the compound of formula (II) with 1,8-naphthalic anhydride in an organic solvent in the presence of a base:

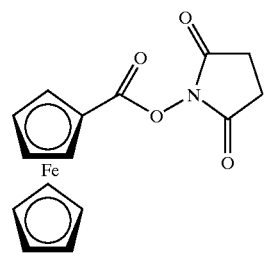

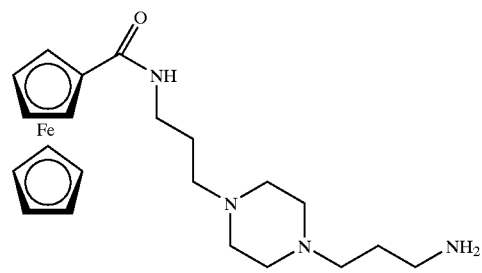

In accordance with still another aspect of the present invention, there is also provided the intermediate compound of formula (II).

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
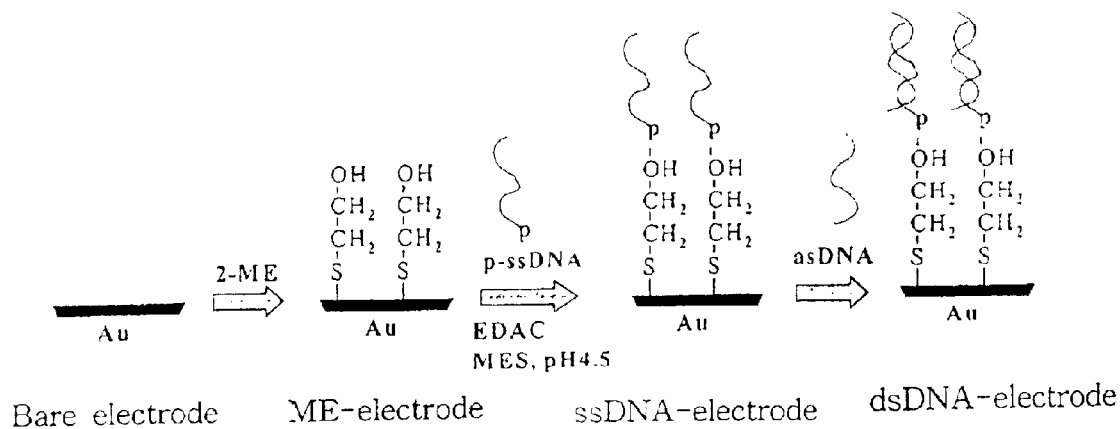
FIG. 1: a schematic procedure for the preparation of a dsDNA-electrode in accordance with one embodiment of the present invention.

The compound of formula (I), N-[[4-(3-ferrocenecarboxamidopropyl)piperazinyl]-propyl]-1,8-naphthalene imide may be prepared in accordance with Scheme 1:

be used as an intercalator in a method for detecting a DNA(target DNA) electrochemically which comprises bringing a single strand of the target DNA into contact with a DNA detection kit containing a single-stranded probe DNA, which is hybridizable with the target DNA and bonded on the surface of an electrode equipped with an output terminal, to obtain a hybridized double strand DNA,

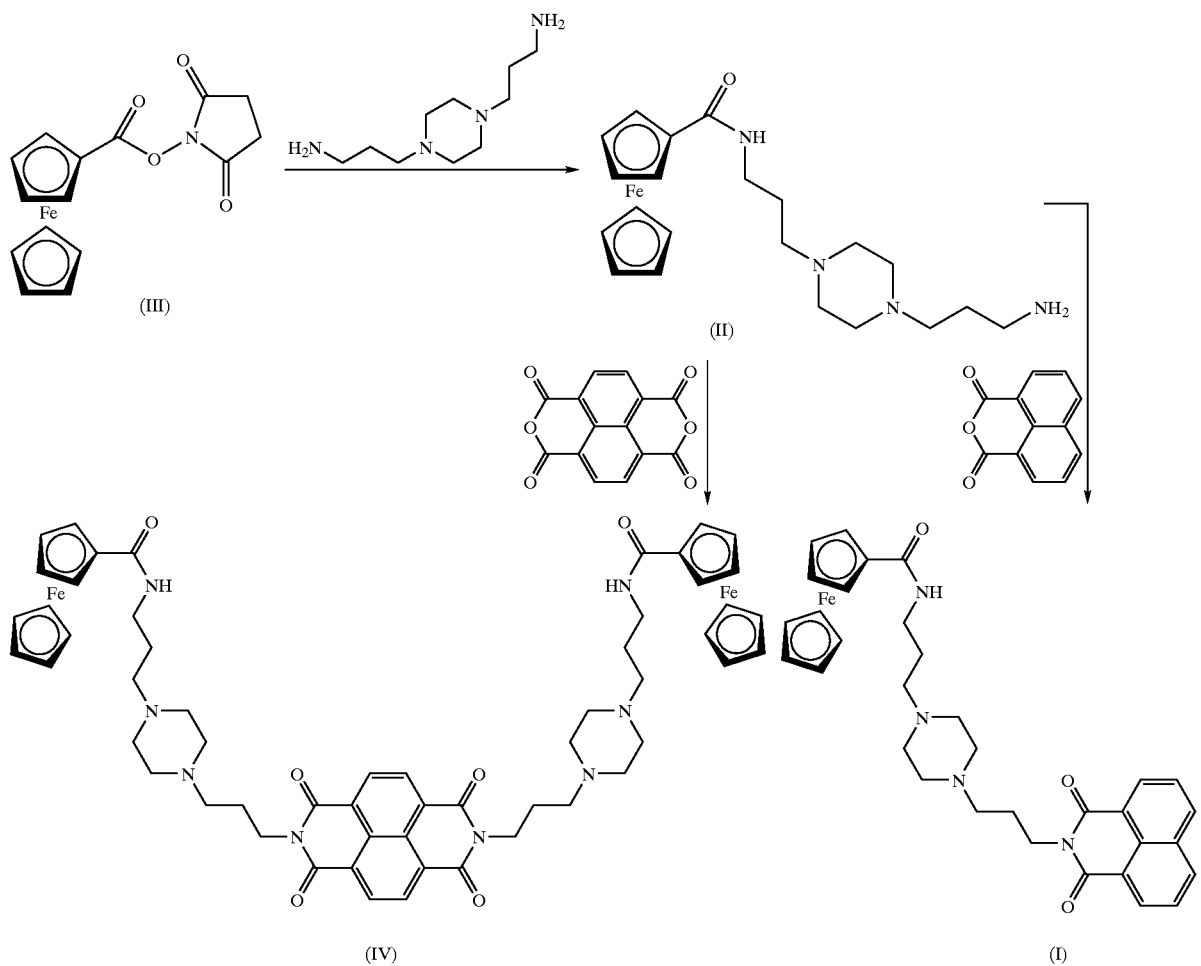

Scheme 1

The compound of formula (III), which may be prepared according to the method disclosed in Anal, Biochem., 218, 436(1994), is reacted with 1,4-bis(3-aminopropyl)piperazine in an organic solvent, i.e., dichloromethane and chloroform to obtain the compound of formula (II). The reaction is carried out at 0 to 40° C., preferably 20 to 25° C. for 5 to 12 hours, preferably 8 to 10 hours.

Then, the compound of formula (II) is reacted with 1,8-naphthalic anhydride in an organic solvent such as isopropylalcohol, benzene and toluene, in the presence of a base, e.g., diisopropylethylamine and triethylamine, to obtain the inventive compound of formula (I). The reaction is carried out at 50 to 110° C., preferably 80 to 85° C. for 4 to 7 hours.

The inventive compound of formula (I) readily intercalates into a double strand DNA and the electron transfer through the intercalated double-stranded DNA is facilitated due to the compound's ferrocene moieties having desirable redox properties. Accordingly, the inventive compound may intercalating the double-stranded DNA with the inventive compound, and determining the current generated when a voltage is applied to the electrode. It is understood that one molecule of the compound of formula (I) intercalates one pair of base.

The sensitivity of DNA detection by the stable method is markedly enhanced when the inventive compound of formula (I) is used together with the compound of formula (IV). This is due to the fact that the compound of formula (IV) (IC1) intercalates selectively into a site which is separated by 3 to 5 pairs of bases from the next site, while the insertion of one molecule of the compound of formula (I) (IC2).

Thus, when a combination of IC1 and IC2 is used in a weight ratio of 1:0.1~10, IC2 is inserted into sites which are not occupied by IC1 and they work together to create a synergistic effect of enhancing the electron transport process through the dsDNA chain. IC2 further acts as a supersensitizer for the reduction of oxidized IC1.

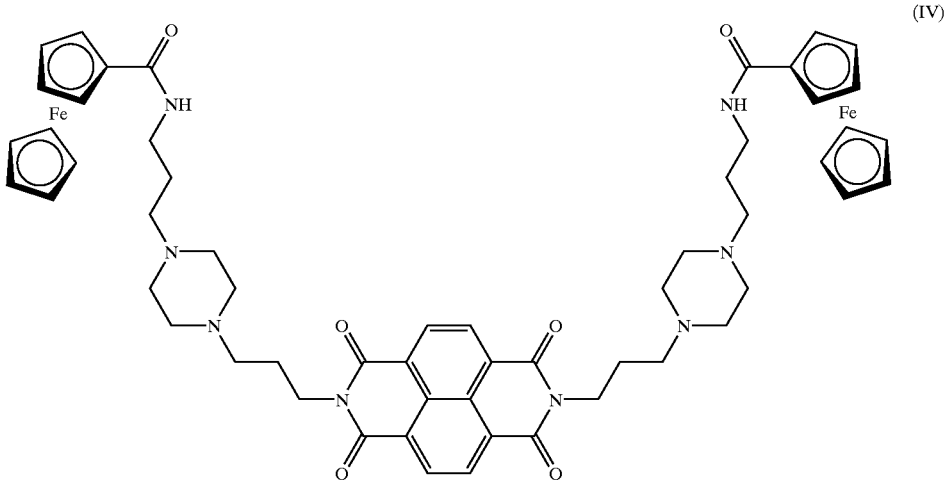

(IV)

The compound of formula (II) may be used as an intermediate in the preparation of the compound of formula (IV) as well as the compound of formula (I). That is, the compound of formula (II) may be reacted with 1,4,5,8-naphthalenetetracarboxylic dianhydride in the presence of a base to obtain the compound of formula (IV) is a high yield.

The following Examples are given for the purpose of illustration only, and are not intended to limit the scope of the invention.

Preparation 1

Preparation of ferrocenecarboxylic acid N-hydroxysuccinimide ester (the compound of formula (III))

According to the preparation method disclosed in Aanl. Biochem., 218, 436(1994), a mixture of 1,000 mg of ferrocenecarboxylic acid(4.35 mmol) and 560 mg of N-hydroxysuccineimide(4.87 mmol) was dissolved in 40 ml of distilled 1,4-dioxane, added 100 mg of dicyclohexylcarbodiimide dissolved in 10 ml of distilled 1,4-dioxane, and stirred for 12 hours under a nitrogen atmosphere. The resulting solution was filtered and the solid thus obtained was purified by silicagel chromatography using a mixture of n-hexane and ethylacetate(1:1, $R_f$=0.40) as an eluent to obtain 1.39 g of the title compound as a light yellow solid (Yield: 99%).

$^1$H NMR(CDCl$_3$; 300 MHz) δ 2.88(4H, br s), 4.39(5H, s), 4.57(2H, m), 495(2H, m) ppm

EXAMPLE 1

Preparation of N-[[4-(3-ferrocenecarboxamidopropyl)piperazinyl]-propyl]-1, 8-naphthalene Imide (the Compound of Formula (I))

(Step 1) Preparation of N-[3-[4-(3-aminopropyl)piperazine-1-yl]propyl] ferroceneamide (the compound of formula (II))

284 μl of 1,4-bis(3-aminopropyl)piperazine(1.376 mmol) dissolved in 14 ml of dichloromethane was added dropwise over 10 hours to 300 mg of the compound (0.917 mmol) prepared in Preparation 1 dissolved in 10 ml of dichloromethane using a syringe. The resulting solution was filtered and the solid thus obtained was purified by silicagel chromatography using a mixture of methanol and ammonium hydroxide(9:1, $R_f$=0.23) as an eluent to obtain 255 mg of the title compound as a yellow solid (Yield: 62%).

$^1$H NMR(CDCl$_3$; 300 MHz) δ 1.65–1.86(4H, m), 2.35–2.80(14H, m), 2.97(1H, m), 3.45(2H, m), 4.20(5H, s), 4.33(2H, br s), 4.69(2H, br s), 6.91(1H, br m) ppm (Step 2) Preparation of N-[[4-(3-ferrocenecarboxamidopropyl)piperazinyl]-propyl]-1,8-naphthalene imide (the compound of formula (I))

A mixture of 41.2 mg of the compound(0.10 mmol) obtained in Step 1 and 26 μl of diisopropylethylamine(0.150 mmol) was dissolved in 10 ml of isopropyl alcohol, 17.8 mg of 1,8-naphthalic anhydride(0.09 mmol) was added thereto, and the mixture was refluxed for 2 hours under a nitrogen atmosphere. Then, the resulting solution was cooled to room temperature, filtered and the brown solid obtained was washed with 2 mg portions of cold isopropyl alcohol three times. Analysis of the solid product by NMR and GC(gas chromatography) established that it is the compound of formula (I) having a purity of over 98%. The solid product was recrystallized from acetone to obtain 49 mg of the title compound(0.083 mmol) as a yellow crystal (Yield: 83%).

$^1$H NMR(CDCl$_3$; 300 MHz) δ 1.71(2H, m), 1.94(2H, m), 2.43(6H, m), 2.53(6H, m), 3.41(2H, q, J=6.0 Hz), 4.15(5H, s), 4.22(4H, br m), 4.68(2H, br s)721(1H, br m), 7.73(2H, dd, J=7.5, 8.1 Hz), 8.19(2H, d, J=8.1 Hz), 8.57(2H, d, J=7.5 Hz) ppm Preparation 2

Preparation of N,N-bis[3-[4-(3-ferrocenecarboxaminopropyl)piperazinyl] propyl]naphthalene-1,4,5,8-tetracarboxylic Acid (the Compound of Formula (IV))

110 mg of the compound(0.267 mmol) of Step 1 of Example 1 and 56 μl of diisopropylethylamine(0.320 mmol) were dissolved in 12 ml of isopropyl alcohol, 28.6 mg of 1,4,5,8-naphthalenetetracarboxylic dianhydride(0.107 mmol) was added thereto, and the mixture was refluxed for 6 hours under a nitrogen atmosphere. Then the mixture was cooled to room temperature, filtered and the brown residue obtained was washed with 2 ml of a cold isopropylalcohol three times. Analysis of the solid product by proton NMR and GC established that it has purity over 98%. The solid product was recrystallized with acetone to obtain 110 mg of the title compound (0.104 mmol) as a yellow crystal (Yield: 97%).

$^1$H NMR(CDCl$_3$) δ 1.72(4H, m), 1.96(4H, m), 2.43(12H, m), 2.57(12H, m), 3.44(4H, m), 4.30(10H, m), 4.32(8H, br s), 4.69(4H, br s), 7.02(2H, m), 8.78(4H, s) ppm

EXAMPLE 2

Preparation of a Probe ssDNA-electrode
(Step 1) Coating of Au Electrode

An Au electrode with an area of 2 mm$^2$ (MF-2014 AUE gold electrode, BAS, IN, USA) was sequentially washed with hot 2 M NaOH for 5 min., and then, with concentrated nitric acid for 5 min., followed by two cycles of ultrasonic-treatment in distilled water, each for 3 min. The electrode was dipped in an aqueous 0.1 M sulfuric acid solution, and the voltage applied thereto was cycled between 0 to 1.5 V (vs. an Ag/AgCl reference electrode) at a rate of 100 mV/s using a voltammetric analyzer (BAS, CV-50W, IN, USA), until the current originating from contaminants was no longer detectable, in order to determine a basal line. The bare electrode thus obtained was treated with 1 mM 2-mercaptoethanol(2-ME) solution for 2 hr. to induce sulfide bond formation between the —SH group of 2-mercaptoethanol and the electrode surface. The resulting electrode was coated with a monolayer of covalently bonded —S—CH$_2$CH$_2$—OH, the terminal —OH group being extended outwards.

(Step 2) Preparation of ssDNA-electrode

Using an oligonucleotide synthesizer, sense and anti-sense oligonucleotides of SEQ ID No: 1 and 2 were prepared, and then, a phosphoric acid group was joined to the 5'-end of the sense oligonucleotide. 1-ethyl-3-(3-dimethylaminopropyl)carbodiimide hydrochloride(EDAC) and the sense oligonucleotide(ssDNA) were dissolved to concentrations of 1 μg/μl and 1 mM, respectively, in a 40 mM 2-(N-morpholino)ethanesulfonic acid (MES) buffer (pH 4.5), and the coated electrode prepared in (Step 1) was treated with the solution for 24 hrs to obtain an ssDNA-electrode having the phosphoric acid groups of the ssDNA bonded with the —OH groups of the electrode surface.

EXAMPLE 3

Detection of DNA
(Step 1) Formation of Hybrid DNA

1 μl of anti-sense DNA (asDNA) (1 nmol/μl) of SEQ ID No:2 was added to 30 μof a hybridizing solution (0.09 μg/μl of salmon spermatozoon DNA, 0.5 μg/μl of acetylized cow serum albumin, 27 mM MES(free acid), 74 mM MES (sodium salt), 0.89M NaCl, 0.01% Tween 20 and 20 mM EDTA), and the ssDNA-electrode prepared in Example 2 was reacted with the solution at 37° C. for 24 hrs to form a hybrid DNA. The resulting electrode was washed with a washing solution (27 mM MES(free acid), 74 mM MES (sodium salt), 26 mM NaCl and 0.01% Tween 20) at 37° C. for 15 min. and the washing procedure was repeated three-times to obtain a dsDNA-electrode which has double-stranded DNAs attached to the electrode. The preparative procedure of such a dsDNA-electrode is schematically shown in FIG. 1.

(Step 2) Combination of dsDNA and Intercalator

N,N-bis[[4-(3-ferrocenecarboxamidopropyl)piperazinyl] propyl]-naphthalene-1,4,5,8-tetracarboxylic acid of formula (IV) (IC1) and N-[[4-(3-ferrocenecarboxamidopropyl) piperazinyl]-propyl]-1,8-naphthalene imide of formula (I) (IC2) were dissolved in distilled water, each to the concentration of 40 μM, and the dsDNA-electrode prepared in (Step 1) was treated with the solution at room temperature for 10 min. to obtain an dsDNA-electrode wherein both IC1 and IC2 were incorporated in the dsDNA as intercalators. For comparison, another dsDNA-electrode intercalated only by IC1 was prepared by a similar method.

Figure 2:
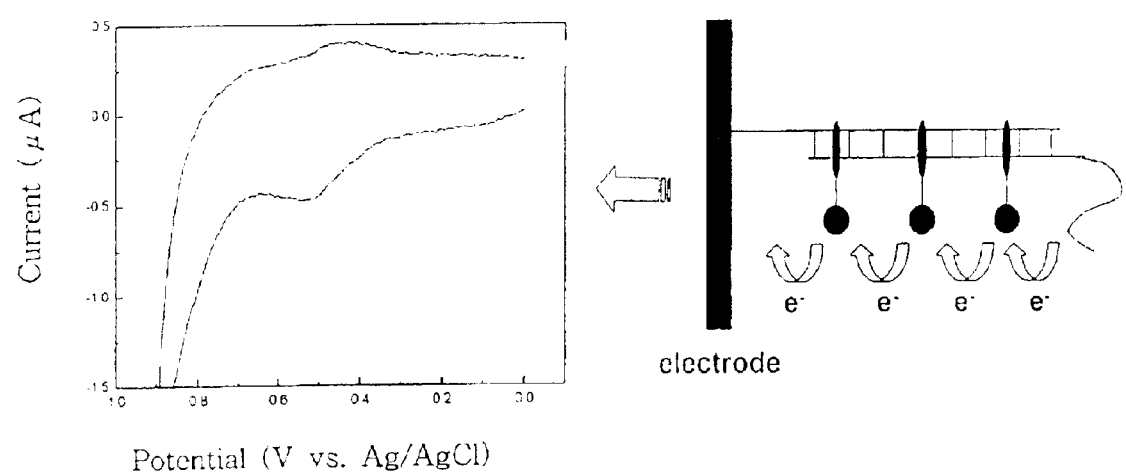
FIG. 2: a schematic representation of the electron transfer through a layer of an intercalator and a typical cyclic current-voltage curve obtained therefor.

A voltage was applied to a tri-electrode system which comprises one of the prepared dsDNA-electrodes as a working electrode, Ag/AgCl as a reference electrode and Pt wire as a counter electrode, and the current generated by the applied voltage-induced redox reactions in the electrolyte solution (0.1 M KCl) was measured with a voltammetric analyzer (BAS, CV-50W, UK). In this case, the current is transferred to the electrode via IC1 and IC2, or via IC1 alone, and the amount of the current was obtained from the cyclic voltammetry (see FIG. 2).

Figure 3:
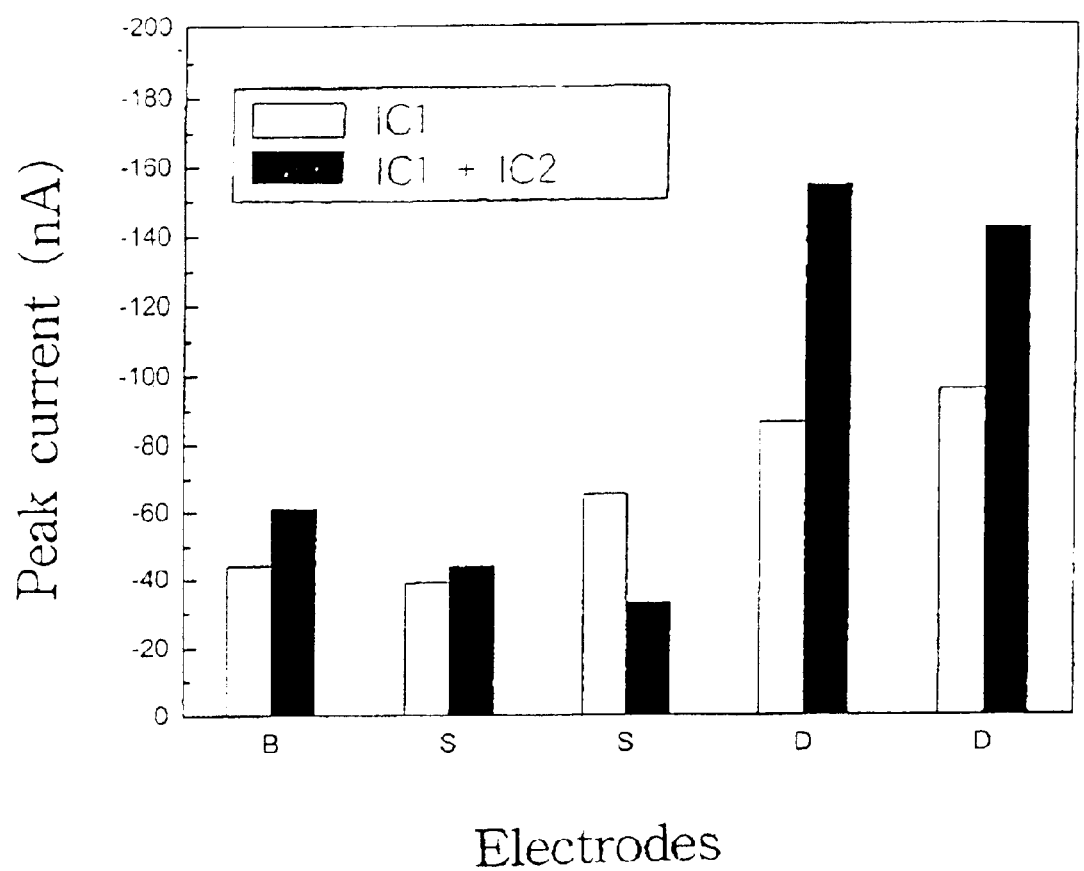
FIG. 3: peak current values obtained with the inventive intercalator and the mixed intercalator.

As shown in FIG. 3, the peak current obtained for the system containing the conventional intercalator, i.e., IC1 alone, was not nearly as high as the currents obtained for two cases of the inventive mixed intercalator (IC1 and IC2). In this figure, B refers to the basal line mentioned in (Step 1) of Example 2; S, an ssDNA-electrode; and D, a dsDNA-electrode (two independent cases). The markedly high current density obtained for the inventive dsDNA-electrode may be attributed to the ability of IC2 to occupy sites inaccessible by IC1.

As described above, in accordance with the present invention, N,N-bis[[4-(3-ferrocenecarboxaminopropyl) piperazinyl]propyl]naphthalene-1,4,5,8-tetra carboxylic acid is capable of enhancing the sensitivity of electrochemical detection of double-stranded DNAs to a remarkably high level, particularly when used in combination with the compound of formula (IV).

While the embodiments of the subject invention have been described and illustrated, it is obvious that various changes and modifications can be made therein without departing from the spirit of the present invention which should be limited only by the scope of the appended claims.

What is claimed is:

1. N-[[4-(3-ferrocenecarboxamidopropyl)piperazifly1]-propyl]-1,8-naphthalene imide of formula (I)

2. A method for the preparation of the compound of claim 1, which comprises reacting the compound of formula (III) with 1,4-bis(3-aminopropyl)piperazine in an organic solvent to obtain the compound of formula (II), and reacting the compound of formula (II) with 1,8-naphtholic anhydride in an organic solvent in the presence of a base

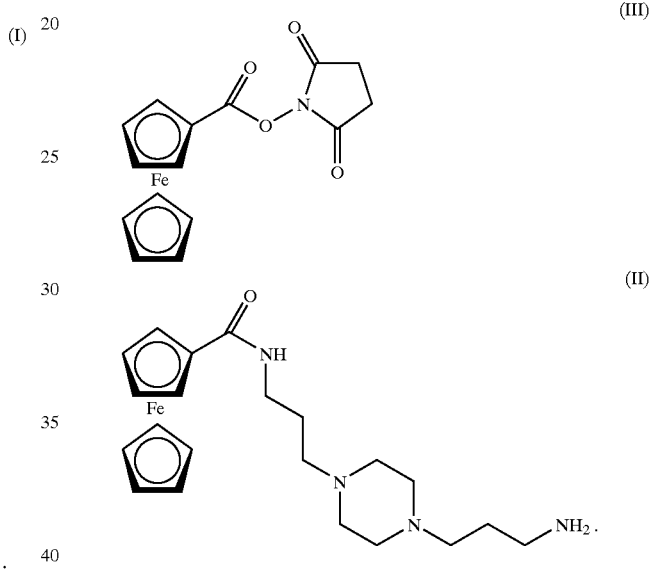

* * * * *

SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<221> NAME/KEY: misc_feature
<223> OTHER INFORMATION: synthetic sense oligonucleotide

<400> SEQUENCE: 1
cctaaccaga tttcaaattt tatctttt                28

```
<210> SEQ ID NO 2
<211> LENGTH: 28
<212> TYPE: DNA
<213> ORGANISM: Artificial Sequence
<220> FEATURE:
<221> NAME/KEY: misc_feature
<223> OTHER INFORMATION: antisense of SEQ ID NO:1

<400> SEQUENCE: 2
aaaagataaa atttgaaatc tggttagg                             28
```